(12) United States Patent
Umbarger et al.

(10) Patent No.: US 11,041,203 B2
(45) Date of Patent: Jun. 22, 2021

(54) METHODS FOR ASSESSING A GENOMIC REGION OF A SUBJECT

(71) Applicant: Molecular Loop Biosolutions, LLC, Cambridge, MA (US)

(72) Inventors: Mark Umbarger, Brookline, MA (US); Gregory Porreca, Cambridge, MA (US)

(73) Assignee: Molecular Loop Biosolutions, Inc., Cambridge, MA (US)

( * ) Notice: Subject to any disclaimer, the term of this patent is extended or adjusted under 35 U.S.C. 154(b) by 953 days.

(21) Appl. No.: 14/512,682

(22) Filed: Oct. 13, 2014

(65) Prior Publication Data

US 2015/0111208 A1   Apr. 23, 2015

Related U.S. Application Data

(60) Provisional application No. 61/892,848, filed on Oct. 18, 2013.

(51) Int. Cl.
*C12Q 1/6883* (2018.01)

(52) U.S. Cl.
CPC ..... *C12Q 1/6883* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,871,921 A | 2/1999 | Landegren et al. |
| 5,993,611 A | 11/1999 | Moroney, III et al. |
| 6,100,099 A | 8/2000 | Gordon et al. |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,197,508 B1 | 3/2001 | Stanley |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,489,105 B1 | 12/2002 | Matlashewski et al. |
| 6,558,928 B1 | 5/2003 | Landegren |
| 6,582,938 B1 | 6/2003 | Su et al. |
| 6,613,516 B1 | 9/2003 | Christians et al. |
| 6,714,874 B1 | 3/2004 | Myers et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |

(Continued)

FOREIGN PATENT DOCUMENTS

| | | |
|---|---|---|
| EP | 1321477 A1 | 6/2003 |
| EP | 1564306 A2 | 8/2005 |

(Continued)

OTHER PUBLICATIONS

Challis et al., 2012, An integrative variant analysis suite for whole exome next-generation sequencing data, BMC Informatics 13(8):1-12.
Liu et al., 2012, Comparison of next-generation sequencing systems, ePub 2012(251364).
Nuttle et al., 2013, Rapid and accurate large-scale genotyping of duplicated genes and discovery of interlocus gene conversions, Nat Methods 10(9): 903-909, and Supplementary Information (58 pages).
Williams, 2003, Restriction Endonucleases Classification, Properties, and Applications, Molecular Biotechnology 23 (3):225-43.

(Continued)

*Primary Examiner* — Joseph Woitach

(74) *Attorney, Agent, or Firm* — Brown Rudnick LLP; Thomas C. Meyers

(57) ABSTRACT

The invention generally relates to method for assessing a genomic region of a subject. In certain embodiments, methods of the invention involve obtaining a sample including nucleic acid from a subject. The nucleic acid includes a target sequence from a target genomic region and a paralogous sequence from a non-target genomic region. The target sequence and the paralogous sequence are isolated from the sample. The target sequence and the paralogous sequence are sequenced to obtain sequence reads that include target sequence reads and paralogous sequence reads. The paralogous sequence reads are excluded, and the genomic region of the subject are assessed based on the target sequence reads.

17 Claims, 2 Drawing Sheets

(56) References Cited

U.S. PATENT DOCUMENTS

| | | |
|---|---|---|
| 6,858,412 B2 | 2/2005 | Willis et al. |
| 6,911,345 B2 | 6/2005 | Quake et al. |
| 6,913,879 B1 | 7/2005 | Schena |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,666,593 B2 | 2/2010 | Lapidus |
| 7,700,323 B2 | 4/2010 | Willis et al. |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,165,821 B2 | 4/2012 | Zhang |
| 8,209,130 B1 | 6/2012 | Kennedy et al. |
| 8,462,161 B1 | 6/2013 | Barber |
| 8,463,895 B2 | 6/2013 | Arora et al. |
| 8,529,744 B2 | 9/2013 | Marziali et al. |
| 8,812,422 B2 | 8/2014 | Nizzari et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0177105 A1 | 9/2003 | Xiao et al. |
| 2003/0203370 A1 | 10/2003 | Yakhini et al. |
| 2003/0224384 A1 | 12/2003 | Sayood et al. |
| 2004/0106112 A1 | 6/2004 | Nilsson et al. |
| 2004/0142325 A1 | 7/2004 | Mintz et al. |
| 2004/0152108 A1 | 8/2004 | Keith et al. |
| 2004/0209299 A1 | 10/2004 | Pinter et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0244879 A1 | 11/2005 | Schumm et al. |
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0166705 A1 | 7/2007 | Milton et al. |
| 2007/0225487 A1 | 9/2007 | Nilsson et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0269068 A1 | 10/2008 | Church et al. |
| 2008/0280955 A1 | 11/2008 | McCamish |
| 2008/0293589 A1 | 11/2008 | Shapero |
| 2009/0019156 A1 | 1/2009 | Mo et al. |
| 2009/0026082 A1 | 1/2009 | Rothberg et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0191565 A1 | 7/2009 | Lapidus et al. |
| 2009/0192047 A1 | 7/2009 | Parr et al. |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0159440 A1 | 6/2010 | Messier et al. |
| 2010/0188073 A1 | 7/2010 | Rothberg et al. |
| 2010/0197507 A1 | 8/2010 | Rothberg et al. |
| 2010/0216151 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0098193 A1 | 4/2011 | Kingsmore et al. |
| 2011/0159499 A1 | 6/2011 | Hindson et al. |
| 2011/0166029 A1 | 7/2011 | Margulies et al. |
| 2011/0230365 A1 | 9/2011 | Rohlfs et al. |
| 2011/0257889 A1 | 10/2011 | Klammer et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0059594 A1 | 3/2012 | Hatchwell et al. |
| 2012/0115736 A1 | 5/2012 | Bjornson et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |

(56) References Cited

U.S. PATENT DOCUMENTS

| | | | |
|---|---|---|---|
| 2012/0252020 | A1 | 10/2012 | Shuber |
| 2012/0252684 | A1 | 10/2012 | Selifonov et al. |
| 2013/0222388 | A1 | 8/2013 | McDonald |
| 2013/0268474 | A1 | 10/2013 | Nizzari et al. |
| 2013/0275103 | A1 | 10/2013 | Struble et al. |
| 2013/0344096 | A1 | 12/2013 | Chiang et al. |
| 2014/0129201 | A1 | 5/2014 | Kennedy et al. |

FOREIGN PATENT DOCUMENTS

| | | |
|---|---|---|
| EP | 2437191 A2 | 4/2012 |
| WO | 1995/011995 A1 | 5/1995 |
| WO | 1996/019586 A1 | 6/1996 |
| WO | 1998/014275 A1 | 4/1998 |
| WO | 1998/044151 A1 | 10/1998 |
| WO | 2000/018957 A1 | 4/2000 |
| WO | 2002/093453 A2 | 11/2002 |
| WO | 2004/018497 | 3/2004 |
| WO | 2004/083819 A2 | 9/2004 |
| WO | 2005/003304 A2 | 1/2005 |
| WO | 2007/010251 A2 | 1/2007 |
| WO | 2007/107717 A1 | 9/2007 |
| WO | 2007/123744 | 11/2007 |
| WO | 2007/135368 A2 | 11/2007 |
| WO | 2009/036525 A2 | 3/2009 |
| WO | 2010/024894 A1 | 3/2010 |
| WO | 2010/126614 A2 | 11/2010 |
| WO | 2012/040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2013/058907 A1 | 4/2013 |
| WO | 2013/191775 A2 | 12/2013 |

OTHER PUBLICATIONS

Wittung, et al., 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu & Aboleneen, 2001, Improved oligonucleotide sequencing by alkaline phosphatase and exonuclease digestions with mass spectrometry, Anal Biochem 290:347-352.
Wu et al., 1998, Sequencing regular and labeled oligonucleotides using enzymatic digestion and ionspray mass spectrometry, Anal Biochem 263:129-138.
Yau, et al., 1996, Accurate diagnosis of carriers of deletions and duplications in Duchenne/Becker muscular dystrophy by fluorescent dosage analysis, Journal Medical Genetics 33(7):550-8.
Ye et al., 2009, Pindel: a pattern growth approach to detect break points of large deletions and medium sized insertions from paired-end short reads, Bioinformatics 25(21):2865-71.
Yoo, et al., 2009, Applications of DNA Microarray in Disease Diagnostics, Journal of Microbiology and Biotechnology 19(7):635-46.
Yoshida, et al., 2004, Role of BRCA1 and BRCA2 as regulators of DNA repair, transcription, and cell cycle in response to DNA damage, Cancer Science 95(11)866-71.
Yu, 2007, A Novel Set of DNA Methylation Markers in Urine Sediments for Sensitive/Specific Detection of Bladder Cancer, Clinical Cancer Research 13(24):7296-7304.
Yuan, 1981, Structure and mechanism of multifunctional restriction endonucleases, Ann Rev Biochem 50:285-319.
Zerbino D.R., et al., 2008, Velvet: algorithms for de novo short read assembly using de Bruijn graphs, Genome Research 18 (5):821-829.
Zhang, et al., 2011, Is Mitochondrial tRNAphe Variant m.593T.Ca Synergistically Pathogenic Mutation in Chinese LHON Families with m.11778G.A? PLOS One 6(10):e26511.
Zhao F., et al., 2009, PGA4genomics for comparative genome assembly based on genetic algorithm optimization, Genomics. 94(4):284-6.
Zheng, et al., 2011, iAssembler: a package for de novo assembly of Roche-454/Sanger transcriptome sequences, BMC Bioinformatics 12:453.
Zimmerman, et al., 2010, A novel custom resequencing array for dilated cardiomyopathy, Genetics in Medicine 12 (5):268-78.
Porreca et al., 2013, Analytical performance of a Next-Generation DNA sequencing-based clinical workflow for genetic carrier screening, American Society of Human Genetics 63rd Annual Meeting, Abstract, Oct. 22, 2013 (2 pages).
Procter, et al., 2006, Molecular Diagnosis of Prader—Willi and Angelman Syndromes by Methylation-Specific Melting Analysis and Methylation-Specific Multiplex Ligation-Dependent Probe Amplification, Clinical Chemistry 52(7):1276-83.
Quail, et al., 2010, DNA: Mechanical Breakage, Encyclopedia of Life Sciences 2010.
Rambaut, et al., 1997, Seq-Gen:an application for the Monte Carlo simulation of DNA sequence evolution along phylogenetic trees, Bioinformatics (formerly CABIOS) 13:235-38.
Richards, 2008, "ACMG recommendations for standards for interpretation and reporting of sequence variations: Revisions 2007," Genet Med 10:294-300.
Richter, et al., 2008, MetaSim—A Sequencing Simulator for Genomics and Metagenomics, PLOS One 3:e3373.
Roberts, 1980, Restriction and modification enzymes and their recognition sequences, Nucleic Acids Res 8(1):r63-r80.
Rodriguez, 2010, "Constructions from Dots and Lines," Bull Am Soc Inf Sci Tech 36(6):35-41, available at http://arxiv.org/pdf/1006.2361.pdf.
Rosendahl, et al., 2013, CFTR, SPINK1, CTRC and PRSS1 variants in chronic pancreatitis: is the role of mutated CFTR over estimated?, Gut 62:585-92.
Rothberg, et al., 2011, An integrated semiconductor device enabling non-optical genome sequencing, Nature 475:348-52.
Rowntree, et al., 2003, The Phenotypic Consequences of CFTR Mutations, Annals of Human Genetics 67:471-85.
S. Gustincich et al., BioTechniques, 1991, 11: 298-302.
Sanger, et al., 1977, DNA sequencing with chain-terminating inhibitors, Proc.National Academy of Science USA 74 (12):5463-7.
Santa Lucia, John Jr., 1998, A unified view of polymer, dumbbell, and oligonucleotide DNA nearest-neighbor thermodynamics, Proc. National Academy of Science USA 95:1460-5.
Sargent, T.D., 1988, Isolation of Differentially Expressed Genes, Methods in Enzymology 152:432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, et al., 2010, A window into third-generation sequencing, Human Molecular Genetics 19(R2):R227-40.
Schatz, et al., 2010, Assembly of large genomes using second-generation sequencing, Genome Res., 20:1165-1173.
Schiffman, 2009, Molecular inversion probes reveal patterns of 9p21 deletion and copy number aberrations in childhood leukemia, Cancer Genetics and Cytogenetics 193:9-18.
Schrijver, et al., 2005, Diagnostic Testing by CFTR Gene Mutation Analysis in a Large Group of Hispanics, The Journal of Molecular Diagnostics 7:289-99.
Schuette et al., 1995, Sequence analysis of phosphorothioate oligonucleotides via matrix-assisted laser desorption ionization time-of-flight mass spectrometry, J. Pharm. Biomed. Anal 13:1195-1203.
Schwartz, et al., 2009, Identification of Cystic Fibrosis Variants by Polymerase Chain Reaction/Oligonucleotide Ligation Assay, The Journal of Molecular Diagnostics 11(3):211-15.
Schwartz, Stuart, 2011, Clinical Utility of Single Nucleotide Polymorphism Arrays, Clinics in Laboratory Medicine 31 (4):581-94.
Sequeira, et al., 1997, Implementing generic, object-oriented models in biology, Ecological Modeling 94.1:17-31.
Sievers F., et al., 2011, Fast, scalable generation of high-quality protein multiple sequence alignments using Clustal Omega, Mol Syst Biol 7:539.

(56) References Cited

OTHER PUBLICATIONS

Simpson, J.T., et al., 2009, ABySS: A parallel assembler for short read sequence data, Genome Res., 19(6): 1117-23.
Slater, G. & Birney, E, 2005, Automated generation of heuristics for biological sequence comparison, BMC Bioinformatics 6:31.
Smirnov et al., 1996, Sequencing oligonucleotides by exonuclease digestion and delayed extraction matrix-assisted laser desorption ionization time-of-flight mass spectrometry, Anal Biochem 238:19-25.
Soni, G. V., & Meller, A, 2007, Progress toward ultrafast DNA sequencing using solid-state nanopores, Clin Chem 53: 1996-2001.
Spanu, P.D., et al., 2010, Genome expansion and gene loss in powdery mildew fungi reveal tradeoffs in extreme parasitism, Science 330(6010): 1543-46.
Strom, 2005, "Mutation detection, interpretation, and applications in the clinical laboratory setting," Mutat Res 573:160-67.
Summerer, Daniel, 2009, Enabling technologies of genomic-scale sequence enrichment for targeted high-throughput sequencing, Genomics 94:363-8.
Sunnucks et al., 1996, Microsatellite and chromosome evolution of parthenogenetic sitobion aphids in Australia, Genetics 144:747-756.
Supplementary European Search Report dated Aug. 26, 2014, for European Patent Application No. 12765217.0, filed Mar. 20, 2012, 5 pages.
Thauvin-Robinet, et al., 2009, The very low penetrance of cystic fibrosis for the R117H mutation: a reappraisal for genetic counselling and newborn screening, Journal of Medical Genetics 46:752-8.
Thompson, et al., 1994, Clustal W: improving the sensitivity of progressive multiple sequence alignment through sequence weighting, position-specific gap penalities and matrix choice, Nucl. Acids. Res., 22:4673-80.
Thompson, et al., 2011, The properties and applications of single-molecule DNA sequencing, Genome Biology 12 (2):217, 10 pages.
Thorstenson, et al., 1998 An automated hydrodynamic process for controlled, unbiased DNA shearing, Genome Res 8:848-855.
Thorvaldsdottir, et al., 2012, Integrative GenomicsViewer (IGV): high-performance genomics data visualization and exploration, Briefings in Bioinformatics 24(2):178-92.
Tokino, 1996, Characterization of the human p57 KIP2 gene: alternative splicing, insertion/deletion polymorphisms in VNTR sequences in the coding region, and mutational analysis, Human Genetics 96:625-31.
Turner et al., 2009, Massively parallel exon capture and library-free resequencing across 16 genomes, Nature Methods 6:315-316.
Turner, et al., 2009, Methods for Genomic Partitioning, Annual Review of Genomics and Human Genetics 10:263-84.
Umbarger et al., 2013, Detecting contamination in Next Generation DNA sequencing libraries, American Society of Human Genetics 63rd Annual Meeting, Abstract, Oct. 22, 2013 (2 pages).
Umbarger, 2014, "Next-generation carrier screening," Genet Med 16:132-40.
Wallace & Miyada, 1987, Oligonucleotide probes for the screening of recombinant DNA libraries, Methods Enzymol 152:432-442.
Wallace, et al., 1979, Hybridization of synthetic oligodeoxyribonucteotides to dp x 174DNA:the effect of single base pair mismatch, Nucleic Acids Research 6:3543-3557.
Warner, et al., 1996, A general method for the detection of large CAG repeat expansions by fluorescent PCR, Journal Medical Genetics 33(12):1022-6.
Warren, R., et al., 2007, Assembling millions of short DNA sequences using SSAKE, Bioinformatics, 23:500-501.
Watson, et al., 2004, Cystic fibrosis population carrier screening: 2004 revision of American College of Medical Genetics mutation panel, Genetics in Medicine 6(5).
Ageno et al., 1969, The alkaline denaturation of DNA, Biophys J 9:1281-1311.
Akhras, M.S., et al., 2007, Connector Inversion Probe Technology: A Powerful OnePrimer Multiplex DNA Amplification System for Numerous Scientific Applications PLOS One 2(9):e915.
Alazard et al., 2002, Sequencing of production-scale synthetic oligonucleotides by enriching for coupling failures using matrix-assisted laser desorption/ ionization time-of-flight mass spectrometry, Analytical biochemistry 301:57-64.
Alazard, et al., 2005, Sequencing Oligonucleotides by Enrichment of Coupling Failures Using Matrix-Assisted Laser Desorption/ Ionization Time-of-Flight Mass Spectrometry, Current Protocols in Nucleic Acid Chemistry 10.10.1-10.10.7.
Albert, 2007, Direct selection of human genomic loci by microarray hybridization, Nature Methods 4(11):903-5.
Aljanabi and Martinez, 1997, Universal and rapid salt-extraction of high quality genomic DNA for PCR-based techniques, Nucl. Acids Res 25:4692-4693.
Antonarakis & the Nomenclature Working Group, 1998, Recommendations for a nomenclature system for human gene mutations, Human Mutation 11:1-3.
Australian Patent Examination Report No. 1 dated Aug. 12, 2014, for Australian Patent Application No. 2010242073, filed Apr. 30, 2010, 4 pages.
Ball, M.P., et al., 2009, Targeted and genome-scale strategies reveal gene-body methylation signatures in human cells, Nature Biotechnology, 27:361-8.
Barany, F, 1991, Genetic disease detection and DNA amplification using cloned thermostable ligase, PNAS, 88:189-193.
Barany, F, 1991, The Ligase Chain Reaction in a PCR World, Genome Research, 1:5-16.
Bau, et al., 2008, Targeted next-generation sequencing by specific capture of multiple genomic loci using low-volume microfluidic DNA arrays, Analytical and bioanalytical chem 393(1):171-5.
Bell et al., 2011, Carrier testing for severe childhood recessive diseases by next-generation sequencing, Science Translational Medicine 3(65ra4), 15 pages
Benner, et al., 2001, Evolution, language and analogy in functional genomics, Trends in Genetics 17:414-8.
Bentzley et al., 1996, Oligonucleotide sequence and composition determined by matrix-assisted laser desorption/ionization, Anal Chem 68:2141-2146.
Bentzley et al., 1998, Base specificity of oligonucleotide digestion by calf spleen phosphodiesterase with matrix-assisted laser desorption ionization analysis, Anal Biochem 258:31-37.
Bickle, Thomas A. & Kruger, Detlev, H., 1993, Biology of DNA Restriction, Microbiological Reviews 57(2):434-50.
Boyden, 2013, High-throughput screening for SMN1 copy number loss by next-generation sequencing, American Society of Human Genetics 63rd Annual Meeting, Abstract, Oct. 22, 2013 (2 pages).
Boyer, 1971, DNA restriction and modification mechanisms in bacteria, Ann Rev Microbiol 25:153-76.
Braasch, et al., 2001, Locked nucleic acid (LNA): ¢ne-tuning the recognition of DNA and RNA, Chemistry & Biology 8 (1):1-7.
Braslaysky, et al., 2003, Sequence information can be obtained from single DNA molecules, Proceedings of the National Academy of Sciences, (USA) 100:3960-4.
Brown, et al., 1979, Chemical synthesis and cloning of a tyrosine tRNA gene, Methods Enzymol., 68:109.
Browne, 2002, Metal ion-catalyzed nucleic Acid alkylation and fragmentation, J Am Chem Soc 124(27):7950-7962.
Brownstein, 2014, "An international effort towards developing standards for best practices in analysis, interpretation and reporting of clinical genome sequencing results in the Clarity Challenge," Genome Biol 15: R53.
Bunyan, et al., 2004, Dosage analysis of cancer predisposition genes by multiplex ligation-dependent probe amplification, British Journal of Cancer, 91(6):1155-59.
Burrow & Wheeler, 1994, A block-sorting lossless data compression algorithm, Technical Report 124, Digital Equipment Corporation, CA.
Castellani, et al., 2008, Consensus on the use and interpretation of cystic fibrosis mutation analysis in clinical practice, Journal of Cystic Fibrosis 7(3):179-96.
Chan et al., 2011, Natural and engineered nicking endonucleases—from cleavage mechanism to engineering of strand-specificity, Nucl Acids Res 39(1):1-18.

(56) References Cited

OTHER PUBLICATIONS

Chennagiri, 2013, A generalized scalable database model for storing and exploring genetic variations detected using sequencing data, American Society of Human Genetics 63rd Annual Meeting, Abstract, Oct. 22, 2013 (2 pages).
Chevreux, B., et al., 1999, Genome Sequence Assembly Using Trace Signals and Additional Sequence Information, Computer Science and Biology: Proceedings of the German Conference on Bioinformatics (GCB) 99:45-56.
Chirgwin, et al., 1979, Isolation of biologically active ribonucleic acid from sources enriched in ribonuclease, Biochemistry, 18:5294-99.
Choe, et al., 2010, Novel CFTR Mutations in a Korean Infant with Cystic Fibrosis and Pancreatic Insufficiency, J Korean Med Sci 25:163-5.
Ciotti, et al., 2004, Triplet Repeat Primed PCR (TP PCR) in Molecular Diagnostic Testing for Friedrich Ataxia, Journal of Molecular Diagnostics 6(4):285-9.
Collins, et al., 2004, Finishing the euchromatic sequence of the human genome, Nature 431.7011:931-45.
Dahl, et al., 2005, Multiplexamplification enabled by selective circularization of large sets of genomic DNA fragments, Nucleic Acids Research 33:e71.
Danecek, 2011, "The variant call format and VCFtools," Bioinformatics 27(15):2156-58.
De la Bastide, M. & McCombie, 2007, W. R., Assembling genome DNA sequences with PHRAP, Current Protocols in Bioinformatics, 17:11.4.1-11.4.15.
Delcher, A.L., et al., 1999, Alignment of whole genomes, Nucleic Acids Research, 27:11.
Deng, et al., 2009, Targeted bisulfite sequencing reveals changes in DNA methylation associated with nuclear reprogramming, nature biotechnology 27:353-60 (and supplement).
DiGuistini, S., et al., 2009, De novo genome sequence assembly of a filamentous fungus using Sanger, 454 and Illumina sequence data, Genome Biology, 10:R94.
Dong, C. & Yu, B., 2011, Mutation Surveyor: An in Silico Tool for Sequencing Analysis, Methods in Molecular Biology 760:223-37.
Dore, et al., 1969, The Alkaline Denaturation of DNA, Biophysical Journal 9(11):1281-1311.
Dudley, et al., 2009, A Quick Guide for Developing Effective Bioinformatics Programming Skills, PLOS Comput Biol 5 (12):e1000589.
Fares, et al., 2008, Carrier frequency of autosomal-recessive disorders in the Ashkenazi Jewish population: should the rationale for mutation choice for screening be reevaluated?, Prenatal Diagnosis 28:236-41.
Faulstich et al., 1997, A sequencing method for RNA oligonucleotides based on mass spectrometry, Anal Chem 69:4349-4353.
Fitch, 1970, "Distinguishing homologs from analogous proteins," Syst Biol 19(2):99-113.
Frey, Bruce, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado et al., 2011, Characterization of large genomic deletions in the FBN1 gene using multiplex ligation-dependent probe amplification, BMC Medical Genetics 12:119 (7 pages).
Garber, 2008, Fixing the front end, Nature Biotechnology 26(10):1101-04.
Gemayel, et al., 2010, Variable Tandem Repeats Accelerate Evolution of Coding and Regulatory Sequences, Annual Review of Genetics 44:445-77.
Glover et al., 1995, Sequencing of oligonucleotides using high performance liquid chromatography and electrospray mass spectrometry, Rapid Com Mass Spec 9:897-901.
Gnirke, et al., 2009, Solution hybrid selection with ultra-long oligonucleotides for massively parallel targeted sequencing, nature biotechnology 27:182-9.

Goto, et al., 2010, BioRuby: bioinformatics software for the Ruby programming language, Bioinformatics 26 (20):2617-9.
Goto, S. A Study on Development of a Deductive Object-Oriented Database and Its Application to Genome Analysis. Diss. PhD Thesis, Kyushu University, 1994.
Gut & Beck, 2995, A procedure for selective DNA alkylation and detection by mass spectrometry, Nucl Acids Res 23 (8):1367-1373.
Hallam, 2014, "Validation for clinical use of, and initial clinical experience with, a novel approach to population-based carrier screening using high-throughput, next-generation DNA sequencing," J Mol Diagn 16:180-89.
Hammond et al., 1996, Extraction of DNA from preserved animal specimens for use in randomly amplified polymorphic DNA analysis, An Biochem 240:298-300.
Hardenbol et al., 2005, Highly multiplexed molecular inversion probe genotyping: over 10,000 targeted SNPs genotyped in a single tube assay, Genome Res 15:269-75.
Hardenbol, et al., 2003, Multiplexed genotyping with sequence-tagged molecular inversion probes, nature biotechnology 21:673-8.
Harris, et al., 2006, Defects Can Increase the Melting Temperature of DNA-Nanoparticle Assemblies, The Journal of Physical Chemistry B 110:16393-6.
Harris, et al., 2008, Single-Molecule DNA Sequencing of a Viral Genome, Science 320:106-9.
Hiatt et al., 2013, Single molecule molecular inversion probes for targeted, high-accuracy detection of low-frequency variation, Genome Research 23:843-54.
Hodges, et al., 2007, Genome-wide in situ exon capture for selective resequencing, nature genetics 29:1522-7.
Holland, et al., 2008, BioJava: an open-source framework for bioinformatics, Bioinformatics 24(18):2096-97.
Huang, et al., 2008, Comparative analysis of common CFTRpolymorphisms poly-T, TGrepeats and M470V in a healthy Chinese population, World J Gastroenterol 14(12)1925-30.
Husemann, P. & Stoye, 2009, Phylogenetic Comparative Assembly, Algorithms in Bioinformatics: 9th International Workshop, pp. 145-156, Salzberg, S., and Warnow, T., Eds. Springer-Verlag, Berlin Heidelberg.
Iqbal, et al., 2012, De novo assembly and genotyping of variants using colored de Bruijn graphs, Nature Genetics, 44 (2):226-233.
Jaijo, et al., 2010, Microarray-Based Mutation Analysis of 183 Spanish Families with Usher Syndrome, Investigative Ophthalmology & Visual Science 51(3):1311-7.
Jensen, 2001, "Orthologs and paralogs—we need to get it right," Genome Biol 2(8):1002-1002.3.
Jones, et al., 2008, Core Signaling Pathways in Human Pancreatic Cancers Revealed by Global Genomic Analyses, Science 321(5897):1801-1806.
Kennedy et al., 2013, Accessing more human genetic variation with short sequencing reads, American Society of Human Genetics 63rd Annual Meeting, Abstract, Oct. 22, 2013 (2 pages).
Kent, W.J., 2002, BLAT-The BLAST-like alignment tool, Genome Research 4: 656-664.
Kircher, et al., 2010, High-througput DNA sequencing—concepts and limitations, Bioassays 32:524-36.
Kirpekar et al., 1994, Matrix assisted laser desorption/ionization mass spectrometry of enzymatically synthesized RNA up to 150 kDa, Nucleic Acids Res 22:3866-3870.
Klein, et al., 2011,LOCAS-A low coverage sequence assembly tool for re-sequencing projects, PLoS One 6(8) article 23455.
Kneen, 1998, "Green fluorescent protein as a noninvasive intracellular pH indicator," Biophys J 74(3):1591-99.
Koboldt et al., 2009, VarScan: variant detection in massively parallel sequencing of individual and pooled samples, Bioinformatics 25:2283-85.
Krawitz, et al., 2010, Microindel detection in short-read sequence data, Bioinformatics 26(6).
Kreindler, J. L., 2010, Cystic fibrosis: Exploiting its genetic basis in the hunt for new therapies, Pharmacology and Therapeutics 125(2):219-29.
Krishnakumar et al., 2008, A comprehensive assay for targeted multiplex amplification of human DNA sequences, PNAS 105:9296-301.

(56) References Cited

OTHER PUBLICATIONS

Kumar, S., et al., 2010, Comparing de novo assemblers for 454 transcriptome data, Genomics 11:571.

Kurtz, S., et al., 2004, Versatile and open software for comparing large genomes, Genome Biology, 5:R12.

Lam, et al., 2008, Compressed indexing and local alignment of DNA, Bioinformatics 24(6):791-97.

Langmead, et al., 2009, Ultrafast and memory-efficient alignment of short DNA sequences to the human genome, Genome Biology, 10:R25.

Larkin M.A., et al., 2007, Clustal W and Clustal X version 2.0, Bioinformatics, 23, 2947-2948.

Lecompte, O., et al., 2001, Multiple alignment of complete sequences (MACS) in the post-genomic era, Gene 270:17-30.

Li & Durbin, 2009, Fast and accurate short read alignment with Burrows-Wheeler transform, Bioinformatics, 25 (14):1754-60.

Li, et al., 2008, SOAP: short oligonucleotide alignment program, Bioinformatics 24(5):713-14.

Li, et al., 2009, SOAP2: an improved ultrafast tool for short read alignment, Bioinformatics 25(15): 1966-67.

Li, et al., 2009, The Sequence Alignment/Map format and SAMtools, Bioinformatics, 2009, 25(16):2078-9.

Li, et al., 2011, Single Nucleotide Polymorphism Genotyping and Point Mutation Detection by Ligation on Microarrays, Journal of Nanoscience and Nanotechnology 11(2):994-1003.

Lin, et al., 2012, Development and evaluation of a reverse dot blot assay for the simultaneous detection of common and beta thalassemia in Chinese, Blood Cells Molecules, and Diseases 48(2):86-90.

Lipman, D.J., et al., 1985, Rapid and sensitive protein similarity searches, Science 227(4693):1435-41.

Llopis, 1998, "Measurement of cytosolic, mitochondrial, and Golgi pH in single living cells with green fluorescent proteins," Proc Natl Acad Sci USA 95(12):6803-08.

MacArthur, 2014, "Guidelines for investigating causality of sequence variaants in human disease," Nature 508:469-76.

Maddalena, 2005, "Technical standards and guidelines: molecular genetic testing for ultra-rare disorders," Genet Med 7:571-83.

Malewicz, 2010, "Pregel: a system for large-scale graph processing," Proc. ACM SIGMOD Int Conf Mgmt Data 135-46.

Mamanova, 2010, Target-enrichment strategies for nextgeneration sequencing, Nature Methods 7(2):111-8.

Margulies, et al., 2005, Genome sequencing in microfabricated high-density picolitre reactors, Nature 437, Supplemental Material, 52 pages.

Margulies, et al., 2005, Genome sequencing in microfabricated high-density picolitre reactors, Nature 437:376-380.

Marras, 1999, Multiplex detection of single-nucleotide variations using molecular beacons, Genetic Analysis: Biomolecular Engineering 14:151.

Maxam & Gilbert, 1977, A new method for sequencing DNA, PNAS 74:560-564.

May, Robert M., 1988, How Many Species Are There on Earth?, Science 241:1441.

McKenna, 2010, "The Genome Analysis Toolkit: a MapReduce framework for analyzing next-generation DNA seqencing data," Genome Res 20(9):1297-1303.

Meyer et al., 2008, Parallel tagged sequencing on the 454 platform, Nature Protocols 3(2):267-78.

Mills, R.E., et al., 2010, Mapping copy number variation by population-scale genome sequencing, Nature 470:59-65.

Minton, et al., 2011, Mutation Surveyor: Software for DNA Sequence Analysis, Methods in Molecular Biology 688:143-53.

Miyazaki et al., 2009, Characterization of deletion breakpoints in patients with dystrophinopathy carrying a deletion of exons 45-55 of the Duchenne muscular dystrophy (DMD) gene, Journal of Human Genetics 54:127-30.

Mockler, et al., 2005, Applications of DNA tiling arrays for whole-genome analysis, Genomics 85:1-15.

Moudrianakis E. N. & Beer M., 1965, Base sequence determination in nucleic acids with the electron microscope, PNAS, 53:564-71.

Mullan, L. J., 2002, Multiple sequence alignment-the gateway to further analysis, Brief Bioinform, 3:303-5.

Nan, et al., 2006, A novel CFTR mutation found in a Chinese patient with cystic fibrosis, Chinese Medical Journal 119 (2):103-9.

Narang, et al., 1979, Improved phosphotriester method for the synthesis of gene fragments, Methods Enzymol., 68:90.

Ng, et al., 2009, Targeted capture and massively parallel sequencing of 12 human exomes, Nature 461(7261):272-6.

Nicholas, H. B. Jr., et al., 2002, Strategies for multiple sequence alignment, Biotechniques 32:572-91.

Nickerson, et al., 1990, Automated DNA diagnostics using an ELISA-based oligonucleotide ligation assay, Proc. National Academy of Science 87:8923-7.

Nielsen, et al., 1999, Peptide Nucleic Acids, Protocols and Applications (Norfolk: Horizon Scientific Press, 1-19).

Nilsson, et al., 2006, Analyzing genes using closing and replicating circles, Trends in Biotechnology 24:83-8.

Ning, Z., et al., 2001, SSAHA: a fast search method for large DNA databases, Genome Research 11(10): 1725-9 (2001).

Nordhoff et al., 1993, Ion stability of nucleic acids in infrared matrix-assisted laser desorption/ ionization mass spectrometry, Nucl Acid Res 21(15):3347-57.

Nordhoff, et al., 2003, Ion stability of nucleic acids in infrared matrix-assisted laser desorption/ionization mass spectrometry, Nucleic Acids Research 21(15):3347-57.

Nuttle et al., 2014, Resolving genomic disorder-associated breakpoints within segmental DNA duplications using massively parallel sequencing, Nature Protocols 9(6):1496-1513.

Oefner et al., 1996, Efficient random sub-cloning of DNA sheared in a recirculating point-sink flow system, Nucleic Acids Res 24(20):3879-3886.

Oka, et al., 2006, Detection of Loss of Heterozygosity in the p53 Gene in Renal Cell Carcinoma and Bladder Cancer Using the Polymerase Chain Reaction, Molecular Carcinogenesis 4(1).

Okoniewski et al., 2013, Precise breakpoint localization of large genomic deletions using PacBio and Illumina next-generation sequencers, Biotechniques 54(2):98-100.

Oliphant, et al., 2002, BeadArray?Technology: Enabling an Accurate, Cost-Effective Approach to High-Throughput Genotyping, Biotechniques Suppl:56-8, 60-1.

Ordahl et al., 1976, Sheared DNA fragment sizing: comparison of techniques, Nucleic Acids Res 3:2985-2999.

Ostrer, et al., 2001, A genetic profile of contemporary Jewish populations, Nature Reviews Cancer 2:891-8.

Owens et al., 1998, Aspects of oligonucleotide and peptide sequencing with MALDI and electrospray spectrometry, Bioorg Med Chem 6:1547-1554.

Parameswaran et al., 2007, A pyrosequencing-tailored nucleotide barcode design unveils opportunities for large-scale sample multiplexing, Nucleic Acids Research 35:e130, Supplementary Material, 18 pages.

Parameswaran, et al., 2007, A pyrosequencing-tailored nucleotide barcode design unveils opportunities for large-scale sample multiplexing, Nucleic Acids Research 35:e130, pp. 1-9.

Pearson W.R., et al., 1988, Improved tools for biological sequence comparison, PNAS 85(8):2444-8.

Pertea, et al., 2003, TIGR gene indices clustering tools (TGICL), Bioinformatics 19(5):651-52.

Pieles et al., 1993, Matrix-assisted laser desorption ionization time-of-flight mass spectrometry: A powerful tool for the mass and sequence analysis of natural and modified oligonucleotides, Nucleic Acids Res 21:3191-3196.

Porreca et al., 2007, Multiplex amplification of large sets of human exons, Nat Methods 4:931-6.

|  | Chr | Intended? | Map Exon 10? |
|---|---|---|---|
| CFTR Exon 10 (Exon 10 Probe) | 7 | Y | Y |
| Paralog 1 (Exon 10 Probe) | 20 | N | Y |
| Paralog 2 (Exon 10 Probe) | 20 | N | Y |

FIG. 1

METHODS FOR ASSESSING A GENOMIC REGION OF A SUBJECT

RELATED APPLICATION

The present application claims the benefit of and priority to U.S. provisional application Ser. No. 61/892,848, filed Oct. 18, 2013, the content of which is incorporated by reference herein its entirety.

FIELD OF THE INVENTION

The invention generally relates to methods for assessing a genomic region of a subject in which the genomic region has other paralogous genomic regions.

BACKGROUND

Information about the genotype of a subject is becoming more important and relevant for a range of healthcare decisions as the genetic basis for many diseases, disorders, and physiological characteristics is further elucidated. Medical advice is increasingly personalized, with individual decisions and recommendations being based on specific genetic information.

For cost-effective and reliable medical and reproductive counseling on a large scale, it is important to be able to correctly and unambiguously identify the allelic status for many different genetic loci in many subjects. Numerous technologies have been developed for detecting and analyzing nucleic acid sequences from biological samples. A commonly used analysis technology is sequencing. Massively parallel DNA sequencing technologies have greatly increased the ability to generate large amounts of sequencing data at a rapid pace.

As sequencing has increased the ability to probe many genomic loci at once, molecular protocols have been developed to selectively enrich for loci of interest. One such protocol uses molecular inversion probes. A molecular inversion probe is composed of a common linker sequence and two unique targeting arms that hybridize to genomic regions flanking a target. In a capture protocol, probes are tiled across a region of a nucleic acid template to ensure overlapping coverage. The hybridized probes are then filled-in with polymerase and the circularized probes are closed with ligase. Following circularization of the probes, the remaining linear (un-captured) genomic DNA is digested away with exonuclease (leaving only the captured targets within the circularized probes). The probes are then sequenced and sequence data is assembled together. That assembled sequence is analyzed for mutations.

Paralogous sequences present a problem for obtaining accurate genotype information about a subject. A paralogous sequence is a sequence in the genome that is identical or nearly identical to a target sequence. However, the paralogous sequence is in a different region of the genome and has a different function than the target sequence. During a capture reaction, such the one described above, a capture probe will hybridize to both the target sequence and the paralogous sequence. Both the target sequence and the paralogous sequence are subsequently sequenced, and the data related to the paralogous sequence is read as being data of the target sequence. Any variant in the paralogous sequence will be interpreted as a variant in the target sequence. Thus, the paralogous sequence contaminates the analysis, making it difficult or impossible to accurately analyze a genomic region this includes sequences that are paralogous to other sequences.

SUMMARY

The invention provides methods that allow accurate sequencing of genomic regions that are paralogous to other genomic regions. Methods of the invention are accomplished by first excluding paralogous sequence reads from obtained sequence data so that only target sequence reads are used in downstream analysis.

In certain aspects, methods of the invention involve obtaining a sample including nucleic acid from a subject. The nucleic acid includes a target sequence from a target genomic region and a paralogous sequence from a non-target genomic region. The target sequence and the paralogous sequence are isolated from the sample. The target sequence and the paralogous sequence are sequenced (e.g., using Sanger sequencing or next generation sequencing on a sequencing instrument) to obtain sequence reads that include target sequence reads and paralogous sequence reads. The paralogous sequence reads are excluded, and the genomic region of the subject are assessed based on the target sequence reads.

Excluding may involve creating a training set of target sequence reads and identifying one or more common variants present in the training set of target sequence reads. The training set may be derived from specific capture or amplification of only target sequences. This can be done, e.g. by specific PCR followed by Sanger sequencing. This training set is used to define the set of common variants that are or are not present in the target sequence. Any common variant observed in the sequence read data that is not present in this training set can be assumed to be of paralogous origin. Next, a frequency of sequence reads containing variants paralogous sequence reads is calculated. These are any variants that are not observed in the training set. Variant paralogous sequence reads to be excluded are defined based on their frequency. Then, paralogous sequence reads are excluded based on the defining step. In that manner, genotype calls are made that are not polluted by the paralogous variants.

Generally, isolating involves conducting an assay that uses molecular inversion probes. A molecular inversion probe is composed of a common linker sequence and two unique targeting arms that hybridize to genomic regions flanking a target. In a capture protocol, probes are tiled across a region of a nucleic acid template to ensure overlapping coverage. The hybridized probes are then filled-in with polymerase and the circularized probe is closed with ligase. Following circularization of the probes, the remaining linear (un-captured) genomic DNA is digested away with exonuclease (leaving only the captured targets within the circularized probes). The probes are then sequenced and sequence data is assembled together. That assembled sequence is analyzed for mutations.

Sequencing may be any technique known in the art, such as sequencing-by-synthesis and single molecule sequencing-by-synthesis. However, any sequencing platform may be used with methods of the invention. In some embodiments, the probes are amplified prior to sequencing. In other embodiments, the probes are sequenced without prior amplification. Commercially available sequencing instruments are sold by Illumina, Roche, 454 Life Sciences, and Life Technologies.

If sequencing is used as the analysis method, then the probes can undergo a standard sequencing workflow prior to being sequencing. Such workflow may involve attaching barcodes and/or sequencing adaptors to the probes prior to sequencing. The probes may or may not be attached to a solid support for sequencing. Exemplary solid supports are flow cells, beads, or any planar substrate.

The analysis method is used to look for mutations in the sequence information, such as a single nucleotide polymorphism (SNP), and insertion, a deletion, an inversion, a translocation, a substitution, or any combination thereof.

BRIEF DESCRIPTION OF THE FIGURES

FIG. 1 is a schematic depicting the problem of capture of target and paralogous sequences in a capture reaction.

DETAILED DESCRIPTION

Figure 2:
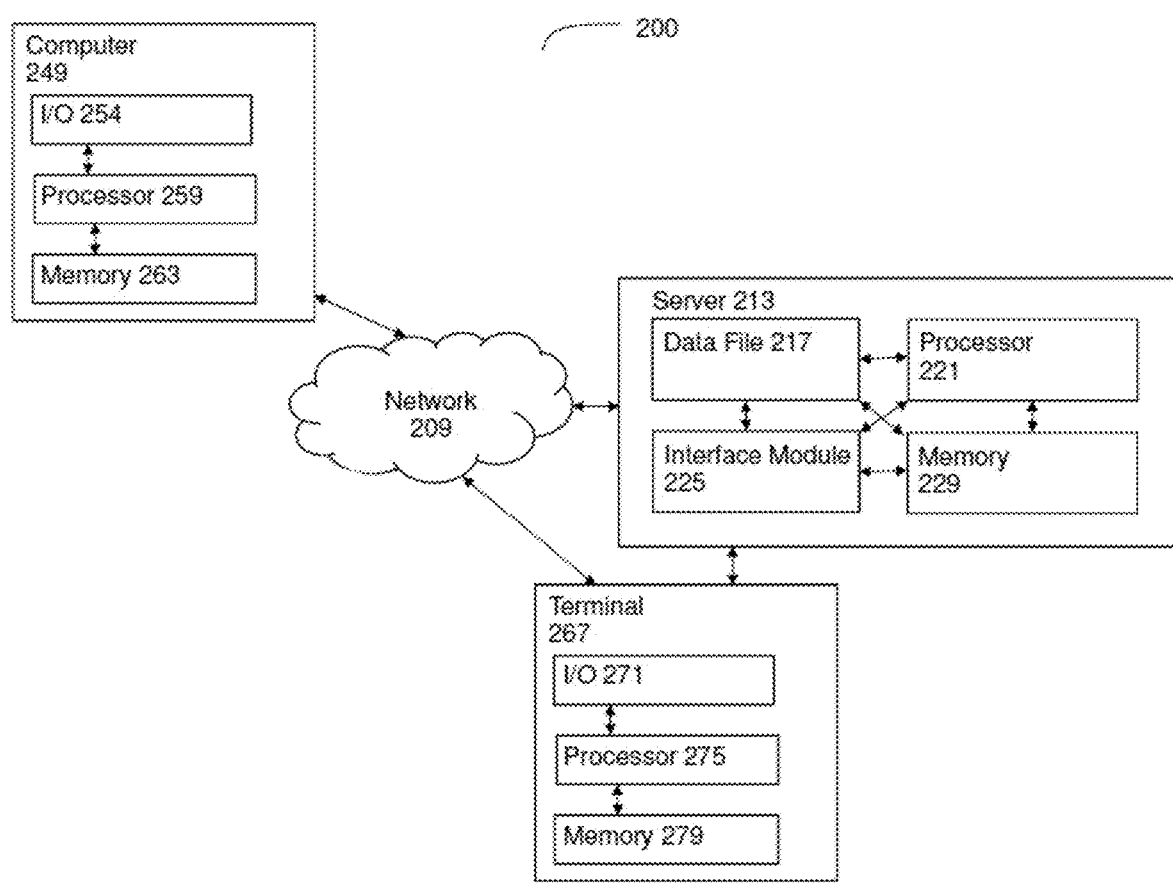
FIG. 2 illustrates a system for performing methods of the invention.

The invention generally relates to method for assessing a target genomic region of a subject in which the target region also has a paralogous region. Paralogous sequences present a problem for obtaining accurate genotype information about a subject. A paralogous sequence is a sequence in the genome that is identical or nearly identical to a target sequence. However, the paralogous sequence is in a different region of the genome and has a different function than the target sequence. FIG. 1 shows how paralogous sequences can be problematic in assessing a genomic region of a subject. FIG. 1 uses exon 10 of the CFTR gene as an example. Exon 10 of CFTR is found on chromosome 7 and is intended for capture. Exon 10 has two paralogous sequences in the genome, both on chromosome 20. Neither paralogous sequence is intended for capture. However, during a capture reaction, such the one shown in FIG. 1, a capture probe will hybridize to the target sequence of Exon 10 of CFTR and also to the paralogous sequences. The target sequence and the paralogous sequences are subsequently sequenced, and the data related to the paralogous sequences are read as being data of the target sequence. Any variant in the paralogous sequence, such as those shown in FIG. 1, is be interpreted as a variant in the target sequence. Thus, the paralogous sequence contaminates the analysis, making it difficult or impossible to accurately analyze a genomic region this includes sequences that are paralogous to other sequences.

Methods of the invention solve the problem of paralogous sequences contaminating analysis of a target genomic region. In certain embodiments, methods of the invention generally involve obtaining a sample including nucleic acid from a subject. The nucleic acid includes a target sequence from a target genomic region and a paralogous sequence from a non-target genomic region. The target sequence and the paralogous sequence are isolated from the sample. The target sequence and the paralogous sequence are sequenced to obtain sequence reads that include target sequence reads and paralogous sequence reads. The paralogous sequence reads are excluded, and the genomic region of the subject are assessed based on the target sequence reads.

Samples

In certain aspects, methods of the invention involve obtaining a sample. The sample is typically a tissue or body fluid that is obtained in any clinically acceptable manner. A tissue is a mass of connected cells and/or extracellular matrix material, e.g. skin tissue, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

Nucleic acid is extracted from the sample according to methods known in the art. See for example, Maniatis, et al., Molecular Cloning: A Laboratory Manual, Cold Spring Harbor, N.Y., pp. 280-281, 1982, the contents of which are incorporated by reference herein in their entirety. See also techniques described in Sambrook, J., Fritsch, E. F., and Maniatis, T. (1989) Molecular Cloning: A Laboratory Manual. 2nd ed. Cold Spring Harbor, N.Y.: Cold Spring Harbor Laboratory), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, Mass.); Beckman Coulter (Brea, Calif.), (AutoGenFlex STAR robot with Qiagen FlexiGene chemistry. For example, Autogen manufactures FlexStar automated extraction kits used in combination with Qiagen FlexiGene Chemistry, and Beckeman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

In certain embodiments, a genomic sample is collected from a subject followed by enrichment for genes or gene fragments of interest, for example by hybridization to a nucleotide array. The sample may be enriched for genes of interest using methods known in the art, such as hybrid capture. See for examples, Lapidus (U.S. Pat. No. 7,666, 593), the content of which is incorporated by reference herein in its entirety. As will be described in more detail below, a preferable capture method uses molecular inversion probes.

RNA may be isolated from eukaryotic cells by procedures that involve lysis of the cells and denaturation of the proteins contained therein. Tissue of interest includes liver cells. RNA may be isolated from fluids of interest by procedures that involve denaturation of the proteins contained therein. Fluids of interest include blood. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX (see Ausubel et al., CURRENT PROTOCOLS IN MOLECULAR BIOLOGY, vol. 2, Current Protocols Publishing, New York (1994). Once bound, poly(A)+mRNA is eluted from the affinity column using 2 mM EDTA/0.1% SDS.

In certain embodiments, the body fluid sample is maternal blood. The maternal blood sample typically will include cell free circulating nucleic acid. That nucleic acid can be a mixture of maternal nucleic acid and fetal nucleic acid from a fetus that is being carried by the subject. Methods for extracting fetal nucleic acid from maternal blood are described for example in Li et al. (J. Amer. Med. Assoc. 293:843-849, 2005) and Lapidus et al. (U.S. patent application publication number 2010/0216151), the content of each of which is incorporated by reference herein its entirety.

In certain embodiments, the sample is a body fluid sample that includes cell free circulating DNA. The sample can be from a male or a female. Cell death, e.g., due to cancer, results in nucleic acid from that cell being shed into the blood stream. That nucleic acid includes the cancerous mutations, and analyzing such nucleic acid provides insight into the subjects cancer.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In a preferred embodiment, the genomic nucleic acid fragments can range from 1 kilobases to 20 kilobases. Preferred fragments can vary in size and have an average fragment length of about 10 kilobases. However, desired fragment length and ranges of fragment lengths can be adjusted depending on the type of nucleic acid targets one seeks to capture and the design and type of MIP probes. The particular method of fragmenting is selected to achieve the desired fragment length. A few non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH (OH— concentration to 0.1N) is added, and the sample is stirred until the DNA redissolves completely. The sample is then incubated at 65 degrees C. for 30 minutes in order to hydrolyze the DNA. Resulting fragments typically range from about 250-1000 nucleotides but can vary lower or higher depending on the conditions of hydrolysis.

In one embodiment, after genomic nucleic acid has been purified, it is resuspended in a Tris-based buffer at a pH between 7.5 and 8.0, such as Qiagen's DNA hydrating solution. The resuspended genomic nucleic acid is then heated to 65 C and incubated overnight. Heating shifts the pH of the buffer into the low- to mid-6 range, which leads to acid hydrolysis. Over time, the acid hydrolysis causes the genomic nucleic acid to fragment into single-stranded and/or double-stranded products.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi:10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point—sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonication is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor®. Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Krü ger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

Capture and Tiling of Target Sequences

Any method known in the art for capturing target sequences may be used with methods of the invention. In certain embodiments, molecular inversion probes (MIP) are used with methods of the invention and an oligonucleotide-driven annealing reaction is performed between genomic DNA and target-specific probes to form open loop complexes, where the target sequence is flanked by the ends of each oligo. Then, polymerase and ligase enzymes are added to fill and seal the gap between the two oligonucleotide probe ends, forming a covalently-closed circular molecule that contains the target sequence. Finally, an exonuclease mix is added to degrade any non-circular DNA (un-reacted probe, genomic DNA). What remains is circular DNA containing the set of targets captured by the reaction. Further details are provided for example in the following U.S. Pat. Nos. 5,866,337; 7,790,388; 6,858,412; 7,993,880; 7,700,323; 6,558,928; 6,235,472; 7,320,860; 7,351,528; 7,074,564; 5,871,921; 7,510,829; 7,862,999; and 7,883,849, the content of each of which is incorporated by reference herein in its entirety. Molecular inversion probes and methods for using such probes is further described, for example in Porreca et al. (Internal patent application publication number WO 2010/126614), the content of which is incorporated by reference herein in its entirety.

Molecular inversion probe technology is used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid template. The molecular inversion probes are introduced to nucleic acid to perform capture of target sequences located on the template. In certain embodiments, the probes are designed such that adjacent probes hybridize to opposite strands of a nucleic acid template. In that manner, that there is less competition between probes for a target region of a nucleic acid template, resulting in more capture events per targeted genomic region and increased capture efficiency.

After capture of the target sequence of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 April 6:1-2).

The result of MIP capture as described above is a library of circular target probes, which then can be processed in a variety of ways. In one aspect, adaptors for sequencing can be attached during common linker-mediated PCR, resulting in a library with non-random, fixed starting points for sequencing. In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

Accordingly, it should be appreciated that in any of the embodiments for molecular inversion probe capture described herein (e.g., tiling/staggering), involve contacting fragmented genomic nucleic acid(s) with one or more different MIP probes. In some embodiments, the amount of genomic nucleic acid used per subject ranges from 1 ng to 10 micrograms (e.g., 500 ng to 5 micrograms). However, higher or lower amounts (e.g., less than 1 ng, more than 10 micrograms, 10-50 micrograms, 50-100 micrograms or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments probes or regions of probes or other nucleic acids are described herein as comprising or including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, etc.).

It should be appreciated that probes, primers, and other nucleic acids designed or used herein may be synthetic, natural, or a combination thereof. Accordingly, as used herein, the term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" may be used interchangeably and refer to oligoribonucleotides as well as oligodeoxyribonucleotides. The terms shall also include polynucleosides (i.e., a polynucleotide minus a phosphate) and any other organic base containing nucleic acid.

The organic bases include adenine, uracil, guanine, thymine, cytosine and inosine. Unless otherwise stated, nucleic acids may be single or double stranded. The nucleic acid may be naturally or non-naturally occurring. Nucleic acids can be obtained from natural sources, or can be synthesized using a nucleic acid synthesizer (i.e., synthetic).

Harvest and isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, or a combination thereof. Non-naturally occurring nucleic acids such as bacterial artificial chromosomes (BACs) and yeast artificial chromosomes (YACs) can also be used.

The invention also contemplates the use of nucleic acid derivatives. As will be described herein, the use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc), chemically-reactive groups including carboxyl, NHS, thiol, etc., or any combination thereof.

A nucleic acid may be a peptide nucleic acid (PNA), locked nucleic acid (LNA), DNA, RNA, or co-nucleic acids of the same such as DNA-LNA co-nucleic acids. PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides in some cases.

PNA are synthesized from monomers connected by a peptide bond (Nielsen, P. E. et al. Peptide Nucleic Acids, Protocols and Applications, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA. Several types of PNA designs exist, and these include single strand PNA (ssPNA), bisPNA and pseudo-complementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., Biochemistry 36:7973 (1997)).

A locked nucleic acid (LNA) is a modified RNA nucleotide. An LNA form hybrids with DNA, which are at least as stable as PNA/DNA hybrids (Braasch, D. A. et al., Chem & Biol. 8(1):1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. Peptide Nucleic Acids, Protocols and Applications, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

While probes have been typically designed to meet certain constraints (e.g. melting temperature, G/C content, etc.) known to partially affect capture/amplification efficiency (Ball et al (2009) Nat Biotech 27:361-8 AND Deng et al (2009) Nat Biotech 27:353-60), a set of constraints which is sufficient to ensure either largely uniform or highly reproducible capture/amplification efficiency has not previously been achieved.

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a by refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule on a nucleic acid fragment (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be necessary to capture multiple subregions of a target nucleic acid in order to analyze the full target.

In some embodiments, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid).

In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Methods of the invention also provide for combining the method of fragmenting the nucleic acid prior to capture with other MIP capture techniques that are designed to increase target uniformity, reproducibility, and specificity. Other MIP capture techniques that can be conducted on fragmented genomic nucleic acids include methods discussed herein and in pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted ('dialed in') by changing the number of different MIPs used to capture a given molecule.

In some embodiments, the 'coverage factor', or number of probes used to capture a basepair in a molecule, is an important parameter to specify. Different numbers of probes per target are indicated depending on whether one is using the tiling approach or one of the staggered approaches.

In a non-limiting embodiment of a tiled probe layout, adjacent probes hybridize to opposite strands of the nucleic acid template. In certain embodiments, a coverage factor of about 3 to about 10 is used. However, the methods are not so limited and coverage factors of up to 2, 3, 4, 5, 6, 7, 8, 9, 10, 20 or more may be used. It is to be appreciated that the coverage factor selected may depend the probe layout being employed. For example, in the tiling approach, for a desired coverage factor, the number of probes per target is typically a function of target length, sub-target length, and spacing between adjacent sub-target start locations (step size). For example, for a desired coverage factor of 3, a 200 bp target with a start-site separation of 20 bp and sub-target length of 60 bp may be encompassed with 12 MIPs. Thus, a specific coverage factor may be achieved by varying the number of probes per target nucleic acid and the length of the molecules captured. In the staggered approach, a fixed-length target nucleic acid is captured as several subregions or as 'super-targets', which are molecules comprising the target nucleic acid and additional flanking nucleic acids, which may be of varying lengths.

The coverage factor will be driven by the extent to which detection bias is tolerable. In some cases, where the bias tolerance is small, it may be desirable to target more subregions of target nucleic acid with, perhaps, higher coverage factors. In some embodiments, the coverage factor is up to 2, 3, 4, 5, 6, 7, 8, 9, 10 or more.

In some embodiments, when a tiled probe layout is used, when the target length is greater than 1 bp and when a step size (distance between the 5'-end of a target and the 5' end of its adjacent target) is less than the length of a target or subregion thereof, it is possible to compute probe number for a particular target based on target length (T), sub target length (S), and coverage factor (C), such that probe number=$T/(S/C)+(C-1)$.

In some aspects, the disclosure provides methods to increase the uniformity of amplification efficiency when multiple molecules are amplified in parallel; methods to increase the reproducibility of amplification efficiency; methods to reduce the contribution of targeting probe variability to amplification efficiency; methods to reduce the effect on a given target nucleic acid of polymorphisms in probe hybridization regions; and/or methods to simplify downstream workflows when multiplex amplification by MIPs is used as a preparative step for analysis by nucleic acid sequencing.

Polymorphisms in the target nucleic acid under the regions flanking a target can interfere with hybridization, polymerase fill-in, and/or ligation. Furthermore, this may occur for only one allele, resulting in allelic drop-out, which ultimately decreases downstream sequencing accuracy. In some embodiments, using a set of MIPs having multiple hybridization sites for the capture of any given target, the probability of loss from polymorphism is substantially decreased because not all targeting arms in the set of MIPs will cover the location of the mutation.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Multiplex amplification strategies disclosed herein may be used analytically, as in detection of SNPs, or preparatively, often for next-generation sequencing or other sequencing techniques. In the preparative setting, the output of an amplification reaction is generally the input to a shotgun library protocol, which then becomes the input to the sequencing platform. The shotgun library is necessary in part because next-generation sequencing yields reads significantly shorter than amplicons such as exons. In addition to the bias-reduction afforded by the multi-tiled approach described here, tiling also obviates the need for shotgun library preparation. Since the length of the capture molecule can be specified when the probes, e.g., MIPs, are designed, it can be chosen to match the read length of the sequencer. In this way, reads can 'walk' across an exon by virtue of the start position of each capture molecule in the probe set for that exon. Reducing analytical errors associated with bias in nucleic acid preparations:

In some embodiments, aspects of the invention relate to preparative steps in DNA sequencing-related technologies that reduce bias and increase the reliability and accuracy of downstream quantitative applications.

There are currently many genomics assays that utilize next-generation (polony-based) sequencing to generate data, including genome resequencing, RNA-seq for gene expression, bisulphite sequencing for methylation, and Immune-seq, among others. In order to make quantitative measurements (including genotype calling), these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. This may include chemical or biochemical treatment of the DNA (e.g., bisulphite treatment), capture of a specific subset of the genome (e.g., padlock probe capture, solution hybridization), and a variety of amplification techniques (e.g., polymerase chain reaction, whole genome amplification, rolling circle amplification).

Systematic and random errors are common problems associated with genome amplification and sequencing library construction techniques. For example, genomic sequencing library may contain an over- or under-representation of particular sequences from a source genome as a result of errors (bias) in the library construction process. Such bias can be particularly problematic when it results in target sequences from a genome being absent or undetectable in the sequencing libraries. For example, an under representation of particular allelic sequences (e.g., heterozygotic alleles) from a genome in a sequencing library can result in an apparent homozygous representation in a sequencing library. As most downstream sequencing library quantification techniques depend on stochastic counting processes, these problems have typically been addressed by sampling enough (over-sampling) to obtain a minimum number of observations necessary to make statistically significant decisions. However, the strategy of oversampling is generally limited to elimination of low-count Poisson noise, and the approach wastes resources and increases the expense required to perform such experiments. Moreover, oversampling can result in a reduced statistical confidence in certain conclusions (e.g., diagnostic calls) based on the data. Accordingly, new approaches are needed for overcoming bias in sequencing library preparatory methods.

Aspects of the disclosure are based, in part, on the discovery of methods for overcoming problems associated with systematic and random errors (bias) in genome capture, amplification and sequencing methods, namely high variability in the capture and amplification of nucleic acids and disproportionate representation of heterozygous alleles in sequencing libraries. Accordingly, in some embodiments, the disclosure provides methods that reduce variability in the capture and amplification of nucleic acids. In other embodiments, the methods improve allelic representation in sequencing libraries and, thus, improve variant detection outcomes. In certain embodiments, the disclosure provides preparative methods for capturing target nucleic acids (e.g., genetic loci) that involve the use of differentiator tag sequences to uniquely tag individual nucleic acid molecules. In some embodiments, the differentiator tag sequence permits the detection of bias based on the frequency with which pairs of differentiator tag and target sequences are observed in a sequencing reaction. In other embodiments, the methods reduce errors caused by bias, or the risk of bias, associated with the capture, amplification and sequencing of genetic loci, e.g., for diagnostic purposes.

Aspects of the invention relate to associating unique sequence tags (referred to as differentiator tag sequences) with individual target molecules that are independently captured and/or analyzed (e.g., prior to amplification or other process that may introduce bias). These tags are useful to distinguish independent target molecules from each other thereby allowing an analysis to be based on a known number of individual target molecules. For example, if each of a plurality of target molecule sequences obtained in an assay is associated with a different differentiator tag, then the target sequences can be considered to be independent of each other and a genotype likelihood can be determined based on this information. In contrast, if each of the plurality of target molecule sequences obtained in the assay is associated with the same differentiator tag, then they probably all originated from the same target molecule due to overrepresentation (e.g., due to biased amplification) of this target molecule in the assay. This provides less information than the situation where each nucleic acid was associated with a different differentiator tag. In some embodiments, a threshold number of independently isolated molecules (e.g., unique combinations of differentiator tag and target sequences) is analyzed to determine the genotype of a subject.

In some embodiments, the invention relates to compositions comprising pools (libraries) of preparative nucleic acids that each comprise "differentiator tag sequences" for detecting and reducing the effects of bias, and for genotyping target nucleic acid sequences. As used herein, a "differentiator tag sequence" is a sequence of a nucleic acid (a preparative nucleic acid), which in the context of a plurality of different isolated nucleic acids, identifies a unique, independently isolated nucleic acid. Typically, differentiator tag sequences are used to identify the origin of a target nucleic acid at one or more stages of a nucleic acid preparative method. For example, in the context of a multiplex nucleic acid capture reaction, differentiator tag sequences provide a basis for differentiating between multiple independent, target nucleic acid capture events. Also, in the context of a multiplex nucleic acid amplification reaction, differentiator tag sequences provide a basis for differentiating between multiple independent, primary amplicons of a target nucleic acid, for example. Thus, combinations of target nucleic acid and differentiator tag sequence (target:differentiator tag sequences) of an isolated nucleic acid of a preparative method provide a basis for identifying unique, independently isolated target nucleic acids.

It will be apparent to the skilled artisan that differentiator tags may be synthesized using any one of a number of different methods known in the art. For example, differentiator tags may be synthesized by random nucleotide addition.

Differentiator tag sequences are typically of a predefined length, which is selected to control the likelihood of producing unique target:differentiator tag sequences in a preparative reaction (e.g., amplification-based reaction, a circularization selection-based reaction, e.g., a MIP reaction). Differentiator tag sequences may be, up to 5, up to 6, up to 7 up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, or more nucleotides in length. For purposes of genotyping, isolated nucleic acids are identified as independently isolated if they comprise unique combinations of target nucleic acid and differentiator tag sequences, and observance of threshold numbers of unique combinations of target nucleic acid and differentiator tag sequences provide a certain statistical confidence in the genotype.

During a library preparation process, each nucleic acid molecule may be tagged with a unique differentiator tag sequence in a configuration that permits the differentiator tag sequence to be sequenced along with the target nucleic acid sequence of interest (the nucleic acid sequence for which the library is being prepared, e.g., a polymorphic sequence). The incorporation of the nucleic acid comprising a differentiator tag sequence at a particular step allows the detection and correction of biases in subsequent steps of the protocol.

A large library of unique differentiator tag sequences may be created by using degenerate, random-sequence polynucleotides of defined length. The differentiator tag sequences of the polynucleotides may be read at the final stage of the sequencing. The observations of the differentiator tag sequences may be used to detect and correct biases in the final sequencing read-out of the library. For example, the total possible number of differentiator tag sequences, which may be produced, e.g., randomly, is $4^N$, where N is the length of the differentiator tag sequence. Thus, it is to be understood that the length of the differentiator tag sequence may be adjusted such that the size of the population of MIPs having unique differentiator tag sequences is sufficient to produce a library of MIP capture products in which identical independent combinations of target nucleic acid and differentiator tag sequence are rare. As used herein combinations of target nucleic acid and differentiator tag sequences, may also be referred to as "target:differentiator tag sequences".

In the final readout of a sequencing process, each read may have an additional unique differentiator tag sequence. In some embodiments, when differentiator tag sequences are distributed randomly in a library, all the unique differentiator tag sequences will be observed about an equal number of times. Accordingly, the number of occurrences of a differentiator tag sequence may follow a Poisson distribution.

In some embodiments, overrepresentation of target:differentiator tag sequences in a pool of preparative nucleic acids (e.g., amplified MIP capture products) is indicative of bias in the preparative process (e.g., bias in the amplification process). For example, target:differentiator tag sequence combinations that are statistically overrepresented are indicative of bias in the protocol at one or more steps between the incorporation of the differentiator tag sequences into MIPs and the actual sequencing of the MIP capture products.

The number of reads of a given target:differentiator tag sequence may be indicative (may serve as a proxy) of the amount of that target sequence present in the originating sample. In some embodiments, the numbers of occurrence of sequences in the originating sample is the quantity of interest. For example, using the methods disclosed herein, the occurrence of differentiator tag sequences in a pool of MIPs may be predetermined (e.g., may be the same for all differentiator tag sequences). Accordingly, changes in the occurrence of differentiator tag sequences after amplification and sequencing may be indicative of bias in the protocol. Bias may be corrected to provide an accurate representation of the composition of the original MIP pool, e.g., for diagnostic purposes.

According to some aspects, a library of preparative nucleic acid molecules (e.g., MIPs, each nucleic acid in the library having a unique differentiator tag sequence, may be constructed such that the number of nucleic acid molecules in the library is significantly larger than the number prospective target nucleic acid molecules to be captured using the library. This ensures that products of the preparative methods include only unique target:differentiator tag sequence; e.g., in a MIP reaction the capture step would under sample the total population of unique differentiator tag sequences in the MIP library. For example, an experiment utilizing 1 ug of genomic DNA will contain about ~150,000 copies of a diploid genome. For a MIP library, each MIP in the library comprising a randomly produced 12-mer differentiator tag sequence (~1.6 million possible unique differentiator tag sequences), there would be more than 100 unique differentiator tag sequences per genomic copy. For a MIP library, each MIP in the library comprising a randomly produced 15-mer differentiator tag sequence (~1 billion possible unique differentiator tag sequences), there would be more than 7000 unique differentiator tag sequences per genomic copy. Therefore, the probability of the same differentiator tag sequence being incorporated multiple times is incredibly small. Thus, it is to be appreciated that the length of the differentiator tag sequence is to be selected based on the amount of target sequence in a MIP capture reaction and the desired probability for having multiple, independent occurrences of target:differentiator tag sequence combinations.

The skilled artisan will appreciate that as part of a MIP library preparation process, adapters may be ligated onto the ends of the molecules of interest. Adapters often contain PCR primer sites (for amplification or emulsion PCR) and/or sequencing primer sites. In addition, barcodes may be included, for example, to uniquely identify individual samples (e.g., patient samples) that may be mixed together. (See, e.g., USPTO Publication Number US 2007/0020640 A1 (McCloskey et al.)

The actual incorporation of the random differentiator tag sequences can be performed through various methods known in the art. For example, nucleic acids comprising differentiator tag sequences may be incorporated by ligation. This is a flexible method, because molecules having differentiator tag sequence can be ligated to any blunt-ended nucleic acids. The sequencing primers must be incorporated subsequently such that they sequence both the differentiator tag sequence and the target sequence. Alternatively, the sequencing adaptors can be synthesized with the random differentiator tag sequences at their 3' end (as degenerate bases), so that only one ligation must be performed. Another method is to incorporate the differentiator tag sequence into a PCR primer, such that the primer structure is arranged with the common adaptor sequence followed by the random differentiator tag sequence followed by the PCR priming sequence (in 5' to 3' order). A differentiator tag sequence and adaptor sequence (which may contain the sequencing primer site) are incorporated as tags. Another method to incorporate the differentiator tag sequences is to synthesize them into a padlock probe prior to performing a gene capture reaction. The differentiator tag sequence is incorporated 3' to the targeting arm but 5' to the amplification primer that will be used downstream in the protocol. Another method to incorporate the differentiator tag sequences is as a tag on a gene-specific or poly-dT reverse-transcription primer. This allows the differentiator tag sequence to be incorporated directly at the cDNA level.

In some embodiments, at the incorporation step, the distribution of differentiator tag sequences can be assumed to be uniform. In this case, bias in any part of the protocol would change the uniformity of this distribution, which can be observed after sequencing. This allows the differentiator tag sequence to be used in any preparative process where the ultimate output is sequencing of many molecules in parallel.

Differentiator tag sequences may be incorporated into probes (e.g., MIPs) of a plurality when they are synthesized on-chip in parallel, such that degeneracy of the incorporated nucleotides is sufficient to ensure near-uniform distribution in the plurality of probes. It is to be appreciated that amplification of a pool of unique differentiator tag sequences may itself introduce bias in the initial pool. However, in most practical cases, the scale of synthesis (e.g., by column synthesis, chip based synthesis, etc.) is large enough that amplification of an initial pool of differentiator tag sequences is not necessary. By avoiding amplification or selection steps on the pool of unique differentiator tag sequences, potential bias may be minimized.

One example of the use of the differentiator tag sequences is in genome re-sequencing. Considering that the raw accuracy of most next-generation sequencing instruments is relatively low, it is crucial to oversample the genomic loci of interest.

Furthermore, since there are two alleles at every locus, it is important to sample enough to ensure that both alleles have been observed a sufficient number of times to determine with a sufficient degree of statistical confidence whether the sample is homozygous or heterozygous. Indeed, the sequencing is performed to sample the composition of molecules in the originating sample. However, after multiple reads have been collected for a given locus, it is possible that due to bias (e.g., caused by PCR amplification steps), a large fraction of the reads are derived from a single originating molecule. This would skew the population of target sequences observed, and would affect the outcome of the genotype call. For example, it is possible that a locus that is heterozygous is called as homozygous, because there are only a few observations of the second allele out of many observations of that locus. However, if information is available on differentiator tag sequences, this situation could be averted, because the over-represented allele would be seen to also have an over-represented differentiator tag sequence (i.e., the sequences with the overrepresented differentiator tag sequence all originated from the same single molecule). Therefore, the sequences and corresponding distribution of differentiator tag sequences can be used as an additional input to the genotype-calling algorithm to significantly improve the accuracy and confidence of the genotype calls.

Barcode Sequences

In certain embodiments, at least one barcode sequence is attached to or incorporated into the isolated probes prior to sequencing. Strategies for barcoding nucleic acid templates are described for example in Porreca et al. (U.S. patent application Ser. No. 13/081,660) and Umbarger et al. (U.S. patent application Ser. No. 13/081,660), the content of each of which is incorporated by reference herein in its entirety. In embodiments that use more than one barcode, the barcode sequences may be attached to the template such that a first barcode sequence is attached to a 5' end of the template and a second barcode sequence is attached to a 3' end of the template. The first and second barcode sequences may be the same, or they may be different. Barcode sequence may be incorporated into a contiguous region of a template that includes the target to be sequenced.

Exemplary methods for designing sets of barcode sequences and other methods for attaching barcode sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; U.S. Pat. Nos. 7,537,897; 6,172,218; and 5,863,722, the content of each of which is incorporated by reference herein in its entirety.

The barcode sequence generally includes certain features that make the sequence useful in sequencing reactions. For example the barcode sequences can be designed to have minimal or no homopolymer regions, i.e., 2 or more of the same base in a row such as AA or CCC, within the barcode sequence. The barcode sequences can also be designed so that they do not overlap the target region to be sequence or contain a sequence that is identical to the target.

The first and second barcode sequences are designed such that each pair of sequences is correlated to a particular sample, allowing samples to be distinguished and validated. Methods of designing sets of barcode sequences is shown for example in Brenner et al. (U.S. Pat. No. 6,235,475), the contents of which are incorporated by reference herein in their entirety. In certain embodiments, the barcode sequences range from about 2 nucleotides to about 50; and preferably from about 4 to about 20 nucleotides. Since the barcode sequence is sequenced along with the template nucleic acid or may be sequenced in a separate read, the oligonucleotide length should be of minimal length so as to permit the longest read from the template nucleic acid attached. Generally, the barcode sequences are spaced from the template nucleic acid molecule by at least one base.

Methods of the invention involve attaching the barcode sequences to the template nucleic acids. Template nucleic acids are able to be fragmented or sheared to desired length, e.g. generally from 100 to 500 bases or longer, using a variety of mechanical, chemical and/or enzymatic methods. DNA may be randomly sheared via sonication, exposed to a DNase or one or more restriction enzymes, a transposase, or nicking enzyme. RNA may be fragmented by brief exposure to an RNase, heat plus magnesium, or by shearing. The RNA may be converted to cDNA before or after fragmentation.

Barcode sequence is integrated with template using methods known in the art. Barcode sequence is integrated with template using, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Barcode sequence can be incorporated via a PCR reaction as part of the PCR primer.

The ligation may be blunt ended or via use of overhanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary over hanging ends are used.

Amplification

Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen Corp.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Methods for performing PCR in droplets are shown for example in Link et al. (U.S. patent application numbers 2008/0014589, 2008/0003142, and 2010/0137163) and Anderson et al. (U.S. Pat. No. 7,041,481 and which reissued as RE41,780), the content of each of which is incorporated by reference herein in its entirety.

Other amplification methods and strategies can also be utilized to detect nucleic acids in biological fluids. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) PNAS 88:189-193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) PNAS 87: 8923-8927).

Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169, 560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Excluding Paralogous Sequences

The below process describes methods for excluding paralogous sequence read data from acquired target sequence read data. The process allows accurate sequencing of genomic regions that are paralogous to other genomic regions. For example, exon 10 of CFTR represents sequence that is paralogous to other sequence in the human genome. Attempting to make accurate genotype calls by sequencing in this region is confounded by contaminating sequence from the paralogous regions. The method, as it applies to the specific CFTR exon 10 problem, is as follows. Note the method is not limited to this one case, but rather is general purpose for any region having paralogous sequence:
1) Define a training set of sequence derived from specific capture or amplification of only CFTR exon 10 (not the paralog(s)). This can be done, e.g. by specific PCR followed by Sanger sequencing. This training set will be used to define the set of common variants that are or are not present in exon 10. Any common variant observed in NGS data which is not present in this training set can be assumed to be of paralogous origin
2) Calculate frequencies of reads containing non-exon 10 variants. These are any variants that are not observed in the training set.
3) Define non-exon 10 reads to exclude based on their frequency.
4) Exclude reads defined in #3 from analysis steps (assembly, alignment, genotyping, etc) which will result in genotype calls that are not polluted by said paralogous variants.

Assembly

Once the paralogous sequence reads are excluded, the target sequence reads are assembled and aligned. Such methods are known in the art, and are described, for example in Kennedy et al. (U.S. Pat. No. 8,209,130), the content of which is incorporated by reference herein it entirety. A contig, generally, refers to the relationship between or among a plurality of segments of nucleic acid sequences, e.g., reads. Where sequence reads overlap, a contig can be represented as a layered image of overlapping reads. A contig is not defined by, nor limited to, any particular visual arrangement nor any particular arrangement within, for example, a text file or a database. A contig generally includes sequence data from a number of reads organized to correspond to a portion of a sequenced nucleic acid. A contig can include assembly results—such as a set of reads or information about their positions relative to each other or to a reference—displayed or stored. A contig can be structured as a grid, in which rows are individual sequence reads and columns include the base of each read that is presumed to align to that site. A consensus sequence can be made by identifying the predominant base in each column of the assembly. A contig according to the invention can include the visual display of reads showing them overlap (or not, e.g., simply abutting) one another. A contig can include a set of coordinates associated with a plurality of reads and giving the position of the reads relative to each other. A contig can include data obtained by transforming the sequence data of reads. For example, a Burrows-Wheeler transformation can be performed on the reads, and a contig can include the transformed data without necessarily including the untransformed sequences of the reads. A Burrows-Wheeler transform of nucleotide sequence data is described in U.S. Pub. 2005/0032095, herein incorporated by reference in its entirety.

Reads can be assembled into contigs by any method known in the art. Algorithms for the de novo assembly of a plurality of sequence reads are known in the art. One algorithm for assembling sequence reads is known as overlap consensus assembly. Overlap consensus assembly uses the overlap between sequence reads to create a link between them. The reads are generally linked by regions that overlap enough that non-random overlap is assumed Linking together reads in this way produces a contig or an overlap graph in which each node corresponds to a read and an edge represents an overlap between two reads. Assembly with overlap graphs is described, for example, in U.S. Pat. No. 6,714,874.

In some embodiments, de novo assembly proceeds according to so-called greedy algorithms. For assembly according to greedy algorithms, one of the reads of a group of reads is selected, and it is paired with another read with which it exhibits a substantial amount of overlap—generally it is paired with the read with which it exhibits the most overlap of all of the other reads. Those two reads are merged to form a new read sequence, which is then put back in the group of reads and the process is repeated. Assembly according to a greedy algorithm is described, for example, in Schatz, et al., Genome Res., 20:1165-1173 (2010) and U.S. Pub. 2011/0257889, each of which is hereby incorporated by reference in its entirety.

In other embodiments, assembly proceeds by pairwise alignment, for example, exhaustive or heuristic (e.g., not exhaustive) pairwise alignment. Alignment, generally, is discussed in more detail below. Exhaustive pairwise alignment, sometimes called a "brute force" approach, calculates an alignment score for every possible alignment between every possible pair of sequences among a set. Assembly by heuristic multiple sequence alignment ignores certain mathematically unlikely combinations and can be computationally faster. One heuristic method of assembly by multiple sequence alignment is the so-called "divide-and-conquer" heuristic, which is described, for example, in U.S. Pub. 2003/0224384. Another heuristic method of assembly by multiple sequence alignment is progressive alignment, as implemented by the program ClustalW (see, e.g., Thompson, et al., Nucl. Acids. Res., 22:4673-80 (1994)). Assembly by multiple sequence alignment in general is discussed in Lecompte, O., et al., Gene 270:17-30 (2001); Mullan, L. J., Brief Bioinform., 3:303-5 (2002); Nicholas, H. B. Jr., et al., Biotechniques 32:572-91(2002); and Xiong, G., Essential Bioinformatics, 2006, Cambridge University Press, New York, N.Y.

Assembly by alignment can proceed by aligning reads to each other or by aligning reads to a reference. For example, by aligning each read, in turn, to a reference genome, all of the reads are positioned in relationship to each other to create the assembly.

One method of assembling reads into contigs involves making a de Bruijn graph. De Bruijn graphs reduce the computation effort by breaking reads into smaller sequences of DNA, called k-mers, where the parameter k denotes the length in bases of these sequences. In a de Bruijn graph, all reads are broken into k-mers (all subsequences of length k within the reads) and a path between the k-mers is calculated. In assembly according to this method, the reads are represented as a path through the k-mers. The de Bruijn graph captures overlaps of length k−1 between these k-mers and not between the actual reads. Thus, for example, the sequencing CATGGA could be represented as a path through the following 2-mers: CA, AT, TG, GG, and GA. The de Bruijn graph approach handles redundancy well and makes the computation of complex paths tractable. By reducing the entire data set down to k-mer overlaps, the de Bruijn graph reduces the high redundancy in short-read data sets. The maximum efficient k-mer size for a particular assembly is determined by the read length as well as the error rate. The value of the parameter k has significant influence on the quality of the assembly. Estimates of good values can be made before the assembly, or the optimal value can be found by testing a small range of values. Assembly of reads using de Bruijn graphs is described in U.S. Pub. 2011/0004413, U.S. Pub. 2011/0015863, and U.S. Pub. 2010/0063742, each of which are herein incorporated by reference in their entirety.

Other methods of assembling reads into contigs according to the invention are possible. For example, the reads may contain barcode information inserted into template nucleic acid during sequencing. In certain embodiments, reads are assembled into contigs by reference to the barcode information. For example, the barcodes can be identified and the reads can be assembled by positioning the barcodes together.

In certain embodiments, assembly proceeds by making reference to supplied information about the expected position of the various reads relative to each other. This can be obtained, for example, if the subject nucleic acid being sequenced has been captured by molecular inversion probes, because the start of each read derives from a genomic position that is known and specified by the probe set design. Each read can be collected according to the probe from which it was designed and positioned according to its known relative offset. In some embodiments, information about the expected position of reads relative to each other is supplied by knowledge of the positions (e.g., within a gene) of an area of nucleic acid amplified by primers. For example, sequencing can be done on amplification product after a number of regions of the target nucleic acid are amplified using primer pairs designed or known to cover those regions. Reads can then be positioned during assembly at least based on which primer pair was used in an amplification that lead to those reads. Assembly of reads into contigs can proceed by any combination or hybrid of methods including, but not limited to, the above-referenced methods.

Assembly of reads into contigs is further discussed in Husemann, P. and Stoye, J, Phylogenetic Comparative Assembly, 2009, Algorithms in Bioinformatics: 9th International Workshop, pp. 145-156, Salzberg, S., and Warnow, T., Eds. Springer-Verlag, Berlin Heidelberg. Some exemplary methods for assembling reads into contigs are described, for example, in U.S. Pat. No. 6,223,128, U.S. Pub. 2009/0298064, U.S. Pub. 2010/0069263, and U.S. Pub. 2011/0257889, each of which is incorporated by reference herein in its entirety.

Computer programs for assembling reads are known in the art. Such assembly programs can run on a single general-purpose computer, on a cluster or network of computers, or on a specialized computing devices dedicated to sequence analysis.

Assembly can be implemented, for example, by the program 'The Short Sequence Assembly by k-mer search and 3' read Extension' (SSAKE), from Canada's Michael Smith Genome Sciences Centre (Vancouver, B. C., CA) (see, e.g., Warren, R., et al., Bioinformatics, 23:500-501 (2007)). SSAKE cycles through a table of reads and searches a prefix tree for the longest possible overlap between any two sequences. SSAKE clusters reads into contigs.

Another read assembly program is Forge Genome Assembler, written by Darren Platt and Dirk Evers and available through the SourceForge web site maintained by Geeknet (Fairfax, Va.) (see, e.g., DiGuistini, S., et al., Genome Biology, 10:R94 (2009)). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Assembly through multiple sequence alignment can be performed, for example, by the program Clustal Omega, (Sievers F., et al., Mol Syst Biol 7 (2011)), ClustalW, or ClustalX (Larkin M. A., et al., Bioinformatics, 23, 2947-2948 (2007)) available from University College Dublin (Dublin, Ireland).

Another exemplary read assembly program known in the art is Velvet, available through the web site of the European Bioinformatics Institute (Hinxton, UK) (Zerbino D. R. et al., Genome Research 18(5):821-829 (2008)). Velvet implements an approach based on de Bruijn graphs, uses information from read pairs, and implements various error correction steps.

Read assembly can be performed with the programs from the package SOAP, available through the website of Beijing Genomics Institute (Beijing, CN) or BGI Americas Corporation (Cambridge, Mass.). For example, the SOAPdenovo program implements a de Bruijn graph approach. SOAP3/GPU aligns short reads to a reference sequence.

Another read assembly program is ABySS, from Canada's Michael Smith Genome Sciences Centre (Vancouver, B. C., CA) (Simpson, J. T., et al., Genome Res., 19(6):1117-23 (2009)). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar, S. et al., Genomics 11:571(2010) and Margulies, et al., Nature 437: 376-380 (2005)). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface.

Cortex, created by Mario Caccamo and Zamin Iqbal at the University of Oxford, is a software framework for genome analysis, including read assembly. Cortex includes cortex_con for consensus genome assembly, used as described in Spanu, P. D., et al., Science 330(6010):1543-46 (2010). Cortex includes cortex_var for variation and population assembly, described in Iqbal, et al., De novo assembly and genotyping of variants using colored de Bruijn graphs, Nature Genetics (in press), and used as described in Mills, R. E., et al., Nature 470:59-65 (2010). Cortex is available through the creators' web site and from the SourceForge web site maintained by Geeknet (Fairfax, Va.).

Other read assembly programs include RTG Investigator from Real Time Genomics, Inc. (San Francisco, Calif.); iAssembler (Zheng, et al., BMC Bioinformatics 12:453 (2011)); TgiCL Assembler (Pertea, et al., Bioinformatics 19(5):651-52 (2003)); Maq (Mapping and Assembly with Qualities) by Heng Li, available for download through the SourceForge website maintained by Geeknet (Fairfax, Va.); MIRA3 (Mimicking Intelligent Read Assembly), described in Chevreux, B., et al., Genome Sequence Assembly Using Trace Signals and Additional Sequence Information, 1999, Computer Science and Biology: Proceedings of the German Conference on Bioinformatics (GCB) 99:45-56; PGA4genomics (described in Zhao F., et al., Genomics. 94(4):284-6 (2009)); and Phrap (described, e.g., in de la Bastide, M. and McCombie, W. R., Current Protocols in Bioinformatics, 17:11.4.1-11.4.15 (2007)). CLC cell is a de Bruijn graph-based computer program for read mapping and de novo assembly of NGS reads available from CLC bio Germany (Muehltal, Germany).

Assembly of reads produces one or more contigs. In the case of a homozygous or single target sequencing, a single contig will be produced. In the case of a heterozygous diploid target, a rare somatic mutation, or a mixed sample, for example, two or more contigs can be produced. Each contig includes information from the reads that make up that contig.

Assembling the reads into contigs is conducive to producing a consensus sequence corresponding to each contig. In certain embodiments, a consensus sequence refers to the most common, or predominant, nucleotide at each position from among the assembled reads. A consensus sequence can represent an interpretation of the sequence of the nucleic acid represented by that contig. Genotyping calls are made from the assembled sequence.

Computing Devices and Software

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data.

Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3 G or 4 G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

In an exemplary embodiment shown in FIG. 2, system 200 can include a computer 249 (e.g., laptop, desktop, or tablet). The computer 249 may be configured to communicate across a network 209. Computer 249 includes one or more processor 259 and memory 263 as well as an input/output mechanism 254. Where methods of the invention employ a client/server architecture, an steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Exemplary step-by-step methods are described. It will be understood that any portion of the systems and methods disclosed herein, can be implemented by computer, including the devices described above. First, sequence reads are obtained from a sequencing instrument that has sequenced the nucleic acid from the subject. This sequence read data is then inputted into the central processing unit (CPU) of a computer. The CPU is coupled to a storage or memory for storing instructions for implementing methods of the present invention. The instructions, when executed by the CPU, cause the CPU to excluding the paralogous sequence reads. The CPU provides this determination by compared the obtained sequence reads against the one or more variant paralogous sequence reads that are to be excluded based on their frequency. If a sequence read matches one of the variant paralogous sequence reads, it is excluded. The variant paralogous sequence read data may be stored locally within the computer, such as within the computer memory. Alternatively, the variant paralogous sequence read data may be stored in a location that is remote from the computer, such as a server. In this instance, the computer communicates across a network to access the variant paralogous sequence read data. The CPU then assessing the genomic region of the subject based on the target sequence reads.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Analysis of Exon 10 of CFTR

An assay was conducted to analyze Exon 10 of CFTR. It was found that capture of Exon 10 of CFTR was difficult due to the fact that Exon 10 of CFTR has two paralogous sequences on chromosome 20. It was found that the molecular inversion probes used to capture Exon 10 of CFTR, also captured the paralogous sequences on chromosome 20. It was determined that the mapping of reads derived from either exon 10 or the paralogous regions were ambiguous and therefore could result in mis-mapping.

To facilitate next generation sequencing (NGS)-based calling of genotypes within exon 10 as part of a CF-only assay, we have developed a read exclusion-based strategy that aims to exclude the reads derived from non-exon 10 sequence from the assembly and genotyping stages of the GATA algorithm. To define the reads to be excluded, we first generated exon 10 Sanger sequencing data for 86 different Coriell samples that had previously been sequenced as part of a research and development CF-only run, utilizing previously designed the primers. We found that with one exception (GM11284, a sample known to contain the common exon 10 c.1364C>A lesion), all of these samples were reference for each base of exon 10. For each of the 85 samples found to be entirely reference across exon 10, we tabulated all of the reads derived from probes designed to capture exon 10 that did not perfectly align to the exon 10 HG18 reference sequence. We then assessed the frequency of these reads across each of the 85 samples and defined those found in greater than 5% of the samples as common non-exon 10 derived reads to be removed by the analysis pipeline prior to assembly and genotyping.

In this study we sought to evaluate the performance of our exon 10 read exclusion strategy on genotyping call accuracy. Thus, using the Sanger primers described above, we performed bi-directional Sanger sequencing on all of the samples included in this study (380 total samples) and we subsequently compared the resulting CF-only genotype calls to those of Sanger (Table 1).

TABLE 1

Summary of the results of the CFTR exon 10 CF-only to Sanger SNV genotype concordance comparisons. Confidence intervals (CI) were calculated using the binconf R function from the Hmisc package and the values presented are the "Wilson" approximation method outputs. Both replicates of GM18799 were not included in this analysis as they both were outright failures. OUC stands for observed uncallable and corresponds to a position that was called in the Sanger data but was not callable in the CF-only data.

| Replicate Number | # TP | # TN | # FP | # FN | # DVG | # OUC | Specificity 95% CI | Sensitivity 95% CI |
|---|---|---|---|---|---|---|---|---|
| 1 | 2 | 70289 | 8 | 0 | 0 | 9 | (0.9997754, 0.9999423) | (0.3423802, 1) |
| 2 | 2 | 70288 | 6 | 0 | 0 | 12 | (0.9997944, 0.9999518) | (0.3423802, 1) |

We observed that all of the Sanger-called non-reference positions were called by the CF-only analysis pipeline and hence we conclude that the sensitivity-based acceptance criterion for this portion of the study was met.

What is claimed is:

1. A method for assessing a genomic region of a subject, the method comprising:

obtaining a sample comprising nucleic acid from a subject, the nucleic acid comprising a target sequence from a target genomic region and a paralogous sequence from a non-target genomic region;

isolating the target sequence and the paralogous sequence from the sample;

sequencing the target sequence and the paralogous sequence to obtain sequence reads that comprise target sequence reads and paralogous sequence reads;

excluding the paralogous sequence reads, wherein excluding comprises:

creating a training set of target sequence reads, wherein the training set is created by:

amplifying of nucleic acids using target-specific primers;

sequencing of resulting amplicons;

identification of variants in amplicon sequences; and defining the training set as comprising the identified variants;

identifying one or more variants observed in the sequence reads that are not present in the training set of target sequence reads as being of paralogous origin;

calculating a frequency of sequence reads comprising variants identified as being of paralogous origin;

defining variant paralogous sequence reads to be excluded based on their calculated frequency; and excluding the defined variant paralogous sequence reads; and assembling and aligning target sequence reads that exclude paralogous sequence reads, based on their frequency, to assess the genomic region of the subject based on the target sequence reads.

2. The method according to claim 1, wherein isolating comprises conducting an assay that uses molecular inversion probes.

3. The method according to claim 2, wherein the assay comprises:

hybridizing said molecular inversion probes to the target sequence the paralogous sequence;

circularizing the hybridized probes;

isolating the circularized probes; and linearizing the circularized probes.

4. The method according to claim 1, wherein sequencing is sequencing by synthesis.

5. The method according to claim 1, wherein the sample is a human body fluid sample.

6. The method according to claim 3, wherein sequencing by synthesis is single molecule sequencing by synthesis.

7. The method according to claim 5, wherein the sample is a maternal blood sample.

8. The method according to claim 7, wherein the maternal blood sample comprises cell free circulating nucleic acid.

9. The method according to claim 8, wherein at least a portion of the cell free circulating nucleic acid is from a fetus being carried the subject.

10. The method according to claim 1, wherein the sample is a human body fluid sample.

11. The method according to claim 10, wherein the body fluid sample comprises cell free circulating nucleic acid.

12. The method according to claim 10, wherein the sample is a maternal blood sample.

13. The method according to claim 12, wherein the maternal blood sample comprises cell free circulating nucleic acid.

14. The method according to claim 13, wherein at least a portion of the cell free circulating nucleic acid is from a fetus being carried the subject.

15. A method for assessing a genomic region of a subject, the method comprising:
   obtaining sequence reads that comprise target sequence reads and paralogous sequence reads;
   excluding the paralogous sequence reads, wherein excluding comprises:
      creating a training set of target sequence reads, wherein the training set is created by:
         amplifying nucleic acids using target-specific primers;
         sequencing of resulting amplicons;
         identification of variants in amplicon sequences; and
         defining the training set as comprising the identified variants;
      identifying one or more variants observed in the sequence reads that are not present in the training set of target sequence reads as being of paralogous origin;
      calculating a frequency of sequence reads comprising variants identified as being of paralogous origin;
      defining variant paralogous sequence reads to be excluded based on their calculated frequency; and
      excluding the defined variant paralogous sequence reads; and
   assembling and aligning target sequence reads that exclude paralogous sequence reads, based on their frequency, to assess a genomic region of a subject based on the target sequence reads.

16. The method according to claim 15, wherein sequencing by is sequencing by synthesis.

17. The method according to claim 16, wherein sequencing by synthesis is single molecule sequencing by synthesis.

* * * * *